(12) United States Patent
Sturr et al.

(10) Patent No.: US 6,228,622 B1
(45) Date of Patent: May 8, 2001

(54) 11-HYDROXYSORDARIN AND A PROCESS FOR PRODUCING IT USING ACTINOMYCES SSP

(75) Inventors: Michael G. Sturr, Mountainside; Michel M. Chartrain, Westfield; Guy H. Harris, Asbury; Jennifer Nielsen-Kahn, East Brunswick; Brian Heimbuch, North Brunswick, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/427,242

(22) Filed: Oct. 26, 1999

Related U.S. Application Data

(60) Provisional application No. 60/105,669, filed on Oct. 26, 1998.

(51) Int. Cl.[7] ............... C12P 19/44; C12N 1/12; A01N 43/04; C07D 315/00
(52) U.S. Cl. ............... 435/74; 514/25; 549/417; 435/252.1
(58) Field of Search ............... 435/74, 252.1; 514/25; 549/417

(56) References Cited

U.S. PATENT DOCUMENTS

| | | |
|---|---|---|
| 5,965,612 | 10/1999 | Tse et al. . |
| 5,972,996 | 10/1999 | Nielsen-Kahn et al. . |

FOREIGN PATENT DOCUMENTS

| | | |
|---|---|---|
| 1162027 | 8/1969 | (GB) . |
| WO 96/14326 | 5/1996 | (WO) . |
| WO 96/14327 | 5/1996 | (WO) . |

OTHER PUBLICATIONS

J. Antibiotics, vol. 48, (1995), pp. 1171–1172, Coval et al.

*Primary Examiner*—Sandra E. Saucier
(74) *Attorney, Agent, or Firm*—Valerie J. Camera; Mark R. Daniel

(57) ABSTRACT

11-hydroxysordarin, biotransformation product of a fermentation with sordarin and Actinomyces spp., (Merck Culture Collection MA7235) ATCC No. 202103 is an antifungal agent. This compound may be useful in the treatment of diseases caused by fungal pathogens such as *Candida albicans*.

7 Claims, No Drawings

11-HYDROXYSORDARIN AND A PROCESS FOR PRODUCING IT USING ACTINOMYCES SSP

This application claims benefit of provisional application 60/105669 filed Oct. 26, 1998.

BACKGROUND OF THE INVENTION

The present invention is directed toward the synthesis of a novel antifungal agent prepared by biotransformation of known compound, sordarin.

Sordarin is an antifungal antibiotic isolated from the ascomycete *Sordaria araneosa* (see GB 1,162,027 and *Helvetica Chimica Acta,* 1971, 51:119–20). Other compounds having the sordarin skeleton have also been reported as antifungal agents. Japanese Kokai J62040292 discloses the compound zofimarin isolated from *Zopfiela marina* sp.; Japanese Kokai J06157582 discloses the compound BE-31405 isolated from Penicillium sp.; and SCH57404 is reported in *J. Antibiotics,* 1995, 48:1171–1172. Semi-synthetic sordarin derivatives are reported in PCT Applications WO96/14326 and WO96/14327. The compounds exhibit antifungal activity against fungi including *Saccharomyces cerevisiae, Candida albicans, C. glabrata* and *C. tropicalis.*

SUMMARY OF THE INVENTION

The present invention is directed toward the synthesis of the novel antifungal compound of the formula

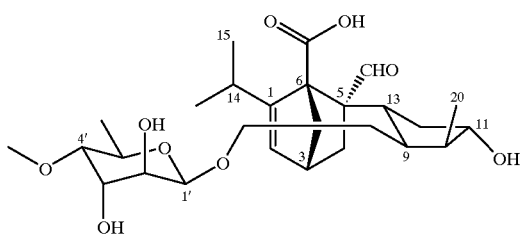

(I)

This compound is prepared by biotransformation of sordarin. The compound has antifungal activity against a number of pathogenic fungi including Candida spp., but is significant because it allows access to a series of sordarin derivatives that are chemically inaccessible.

This invention also relates to a process for the preparation of the compound by fermentation of Actinomyces spp. MA7235, ATCC No. 202103 in the presence of the substrate compound sordarin.

The invention also relates to pharmaceutical compositions containing a therapeutically effective amount of compound I in combination with a pharmaceutically acceptable carrier or excipient.

Additionally, the invention relates to a method of treatment of diseases caused by certain fungal pathogens.

DETAILED DESCRIPTION OF THE INVENTION

There is disclosed compound I of the formula

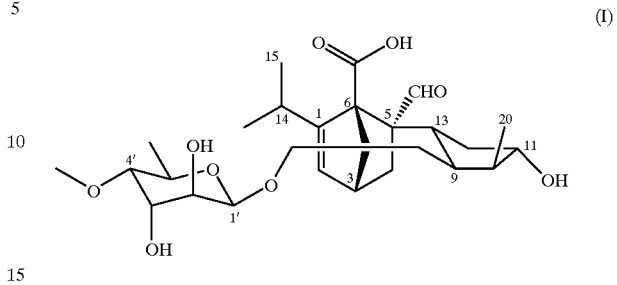

(I)

or a pharmaceutically acceptable salt or hydrate thereof which can be produced by a biotransformation process. The compound of the present invention is prepared by fermentation of the microorganism Actinomyces spp. MA7235, ATCC No. 202103 in the presence of the substrate compound, sordarin, of the formula:

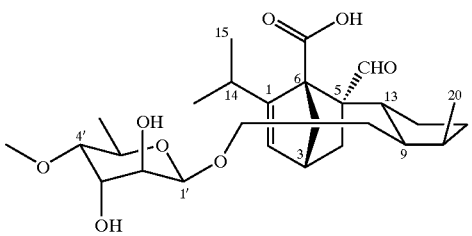

under appropriate conditions.

A sample of the microorganism Actinomyces sp. has been deposited under the Budapest Treaty in the culture collection of the American Type Culture Collection, 10801 University Boulevard, Manassas, Va. 20110-2209, on Apr. 1, 1998 and assigned accession number ATCC 202103.

MA7235 can be generally described as follows. Observations of growth, and general cultural characteristics were made in accordance with the methods of Shirling and Gottleib (International J. System. Bacteriol. 16:313–340). Chemical composition of the cells was determined using the methods of Lechevalier and Lechevalier (in Actinomycete Taxonomy, A. Dietz and D. W. Thayer, Ed. Society for Industrial Microbiology, 1980). Whole Cell Fatty Acids were derivatrized and analyzed as methyl esthers (Fames) by Gas Chromatography by the procedure of Miller and Berger using as MIDI Microbial Identification system (Microbial Identification Systems, Newark, Del.). Coloration of the culture was determined by comparison with color standards in the Munsell color charts (Macbeth Division of Kollmorgen Instruments Corp. P.O. Box 230 Newburgh, N.Y. 12551-0230).

Analysis of Whole Cell Extracts

Peptidoglycan contains Meso-diaminopimelic acid and whole cell extracts contain arabinose, galactose, and rhamnose.

General Growth Characteristics

Good growth on yeast malt extract agar (YME) and Czapeks agar (CZ). Moderate growth on Oatmeal Agar and Glycerol Asparagine agar (Gas). Poor growth on Inorganic Salt Starch agar (ISS) and water agar supplemented with NZ-Amine A (table 1).

Colony Morphology (Oatmeal Agar at 21 Days)

No aerial mycelium. The substrate mycelium is orange in color (7.5YR/7/8) and has a leathery texture.

Micromorphology

Highly branched vegetative hyphae. No aerial hyphae was observed and no spore structures were observed.

Whole Cell Fatty Acid Analysis

FAME analysis revealed that whole cell extracts contained major amounts of 16:0 ISO, 16:0 ISO 2 OH, and 17:1 Cis 9 fatty acids (table 2).

Conclusions

Whole cell analysis reveals that MA7235 has a type IV cell wall. Microscopic observations reveal that MA7235 is filamentous but produces no distinguishing characteristics. Those strains that have type IV cell wall are reported to belong to the Nocaridaceae and Nocardioform bacteria (7). MA7235 does not contain Tuberculasteric acid and thus can not be considered a member of the Nocardiaceae. MA7235 does not share any phenotypic properties with the Nocardioforms and does not group with them by fatty fatty acid analysis. Therefore, an identification of Actinomycetes sp. will be assigned to MA7235.

TABLE 1

Cultural Characteristics of MA7235 at 21 days

| Medium | Growth | Spore structure | Aerial mycelium color | Reverse Color |
|---|---|---|---|---|
| Yeast Malt Extract agar | good | no spore structure observed | no aerial mycellium | Orange (7.5YR/6/8) |
| Glycerol Asparagine agar | moderate | no spore structure observed | no aerial mycellium | Orange (7.5YR/6/8) |
| Inorganic Salt Starch agar | poor | no spore structure observed | no aerial mycellium | Orange (10YR/7/8) |
| Oatmeal agar | moderate | no spore structure observed | no aerial mycellium | Orange (10YR/7/8) |
| Czapeks agar | good | no spore structure observed | no aerial mycellium | Orange (7.5YR/6/8) |
| Water agar | poor | no spore structure observed | no aerial mycellium | Orange |

ND- No colors to report

TABLE 2

Percent of fatty acids in whole cell extracts

| Fatty Acid | Percent in whole cell extracts |
|---|---|
| 14:0 ISO | 0.88% |
| 15: ISO | 4.73% |
| 15:0 Anteiso | 0.68% |
| 15:1 B | 1.99% |
| 15:0 | 2.56% |
| 16:1 ISO H | 2.85% |
| 16:0 ISO | 33.13% |
| 16:1 CIS 9 | 1.54% |
| 16:0 | 1.31% |
| 16:0 10 methyl | 1.40% |
| 17:0 ISO | 1.75% |
| 17:0 Anteiso | 3.12% |
| 17:1 CIS 9 | 12.54% |
| 16:0 ISO 2OH | 14.74% |
| 17:0 | 5.79% |
| 17:0 ISO 10 Methyl | 1.62% |
| 17:0 10 Methyl | 7.86% |
| 17:0 Anteiso 2 OH | 1.31% |

The present invention can be practiced with any strain of Actinomycetes sp. capable of producing compound I and particularly preferred is the ATCC No. 202103 strain.

In general, compound I may be produced by culturing the above described microorganism in the presence of an appropriate concentration of substrate compound sordarin in an aqueous nutrient medium containing sources of assimilable carbon and nitrogen.

Substrate compound sordarin can be obtained as previously described or by synthetic organic procedures.

The compound has antimicrobial properties and may be useful for controlling systemic and superficial fungal infections in humans. Additionally, the compound exhibits activity against certain plant fungal pathogens and may be useful as a broad spectrum crop antifungal agent.

The compound of this invention has antimicrobial properties and is especially useful as a new platform for antifungal agents and organisms causing systemic human pathogenic mycotic infections such as Candida sp. and *Cryptococcus neoformans*. These properties may be effectively utilized by administering compositions containing an antifungal amount of the compound to an area, object or subject, on or in which fungi are to be controlled. Thus, compositions containing an antifungally effective amount of the compound and their use for the control of fungi are aspects of the present invention. Especially preferred aspects of the present invention are compositions in a pharmaceutically acceptable carrier and their use for the control of mycotic infections by administering a therapeutically effective amount of the compound Compound I may be useful as an antifungal agent, especially as an antimycotic agent, which may be demonstrated with the compound in a broth microdilution assay for the determination of minimum inhibitory concentration (MIC). The compound is found to be effective in the assay against fungi selected for their resistance/susceptibility to known compounds, animal virulence, source and clinical importance, at concentrations comparable to an established antifungal agent, amphotericin B.

In the microbroth dilution assay, microorganisms were selected by inoculating 5 milliliters of YNBD broth (yeast nitrogen base with 2% dextrose; Difco) with 50 microliters of yeast culture stored as a 20% glycerol stock at −76° C., or by streaking a yeast culture on Sabouraud dextrose agar (SDA) and incubating for 24–48 hours at 35–37° C. Three to five characteristic colonies were selected and transferred to a fresh plate and incubated under similar conditions. From the regrowth, 3 to 5 colonies were selected and suspended in 5 milliliters of YNBD broth. The liquid cultures were incubated for 16 hours at 35–37° C. in a rollerdrum turning at 56 rpm. The 16 hour broth cultures were adjusted optically to $OD_{600}$ of 0.01 by dilution in YNBD and incubated for 5 hours at 35–37° C. in a rollerdrum turning at 56 rpm. The cultures were further diluted in YNBD to $OD_{600}$ of 0.0014, resulting in a concentration of $1-5 \times 10^4$ cfu/ml which was used as inocula.

The test compound was dissolved at 128 μg/ml in 20% methanol and diluted two-fold in YNBD to achieve a concentration of 64 μg/ml at 10% methanol in the first well of a 96-well, U-bottomed plate. Compounds in column 1 were subsequently serially diluted two-fold and 75 ml of cell suspension was added to each well resulting in an additional two-fold dilution of compound to yield concentrations from 32 mg/ml to 0.0075 mg/ml.

Sordarin, the control compound, was prepared as described above for Compound I.

The plates containing the diluted compounds and cell inocula were incubated for 48 hours at 35–37° C. with MIC (minimum inhibitory concentration) determinations carried out after 24 hours and 48 hours of incubation. Growth and sterility controls for each organism and sterility checks for the compounds also were carried out.

| Compound I | MIC24 |
|---|---|
| C. albicans | 100 μg/ml |

In view of the activity, the compound of the present invention, either singly or as a mixture, is adaptable to being utilized in various applications of antifungal compositions. In such case, compounds may be admixed with a biologically inert carrier, generally with the aid of a surface active dispersing agent, the nature of which would vary depending on whether the use is for the control of pathogens infecting man or animals, or for control of fungi in agriculture such as in soil or plant parts, or for the control of fungi in inanimate objects.

In compositions for medical applications, the compound may be admixed with a pharmaceutically acceptable carrier, the nature of which will depend on whether the composition is to be topical, parenteral or oral.

If said application is to be topical, the drug may be formulated in conventional creams and ointments such as white petrolatum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by mixing the component drugs with any of the usual pharmaceutical media, including for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricants such as calcium stearate, together with binders, disintegrating agents and the like. Water is the preferred liquid carrier for the compound of the invention.

These compositions are then administered in amounts sufficient to obtain the desired antifungal effect. For medical applications, the method comprises administering to a subject in need of treatment a therapeutically effective antifungal amount of the compounds. The appropriate dose will vary depending on age, severity, body weight and other conditions. For topical application, the compositions are applied directly to the area where control is desired. For internal administration, the composition may be applied by injection or may be administered orally.

For non-medical application, the product of the present invention, either alone or as a mixture, may be employed in compositions in an inert carrier which included finely divided dry or liquid diluents, extenders, fillers, conditioners and excipients, including various clays, diatomaceous earth, talc, and the like or water and various organic liquids such as lower alkanols, such as ethanol and isopropanol.

Compositions for injection, a preferred route of delivery, may be prepared in unit dosage form in ampules, or in multidose containers. The injectable compositions may take such forms as suspensions, solutions, or emulsions in oily or aqueous vehicles, and may contain various formulating agents Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ dosage amounts in the range of from about 250 mg to 1000 mg. In parenteral administration, the unit dosage will typically include the pure compound in sterile water solution or in the form of a soluble powder intended for solution, which can be adjusted to neutral pH and isotonic.

The preferred methods of administration of the antifungal compounds include oral and parenteral, e.g., i.v. infusion, i.v. bolus and i.m. injection.

The following examples are provided for the purpose of illustrating the present invention and shall not be construed as limiting the scope or spirit of the invention.

EXAMPLE 1

Flask Bioconversion of Sordarin

A frozen glycerol suspension of Actinomyces spp. MA7235 was inoculated into 25 ml of the preferred production medium (BASA 10 g/L glucose, 20 g/L yeast extract, 20 g/L Hycase, 2.0 g/L $KNO_3$, 0.5 g/L NaCl, 0.5 g/L MgSO$_4$, 0.02 g/L CuCl, 0.025 g/L FeSO$_4$, 0.01 g/L ZnSO$_4$, 0.005 g/L MnSO$_4$, pH to 7.0 with HCl) in a 250 ml flask, incubated aerobically for three days at 29° C. on a rotary shaker operated at 200 rpm. A milliliter of the three day seed culture was passed to 25 ml of fresh production medium and the culture grown under the same conditions for 20–28 hours to a culture pH between 7.2 and 8.0. Sordarin dissolved in 80% was added to a final concentration of 0.5 g/L. The charged broth was extracted 1:1 with methanol and centrifuged to remove cell debris prior to the HPLC analysis. The presence of the Compound I, 11-hydroxysordarin peak was detected by 24 hours postcharging of the broth by reverse phase HPLC separation of the broth. A Phenomenex Primesphere column was used to achieve the separation which was performed on a Spectraphysics HPLC system utilizing a gradient of acetonitrile and acidified water (0.1% H$_3$PO$_4$). The gradient employed was 10% to 60% acetonitrile and the detector was set to 220 nm.

Compound I $^{13}$C NMR (CD3OD): δ 14.2, 18.4, 21.5, 23.0, 28.9, 30.1, 30.2, 38.02, 40.1, 41.9, 43.6, 47.5, 57.1, 59.8, 68.1, 69.9, 72.2, 73.6, 75.9, 81.1, 81.2, 100.1, 132.1, 149.9, 175.3, 205.9.

$^1$H NMR (CD3OD): δ 0.856 (d, 6.5, H-20), 0.979 (d, 6.5, H-15), 1.044 (d, 7.0, H-16), 1.248 (d, 6.0, H-6'), ~1.25 (mult, H-4a), ~1.75 (mult, H-8a), 1.848 (mult, H-10), 2.000 (dd, 4.5, 12.5, H-4b), 2.05–2.113(3H mult, H-8b, 9, 13), 2.330 (mult, H-14), 2.384 (mult, H-12), 2.835 (dd, 4.0, 4.0, H-3), 3.132 (dd, 3.0, 9.5, H-4), 3.376 (s, H-7'), 3.69–3.75 (3H mult, H-2', 5', 19a), 3.838 (ddd, <1, 5.5, 5.5, H-11), 3.914 (d, 9.5, H-19b), 4.115 (dd, 4.0, 4.0, H-3'), 4.587 (d, 1.0, H-1'), 6.127 (dd, 1.0, 3.0, H-2), 9.636 (s, H-17).

Mass spectra were recorded on a Jeol SX-102A (electron impact, EI,90 eV) and TSQ700 (LC-MS-ESI, Liquid chromatography-Electrospray ionization) mass spectrometers. Exact mass measurements were performed at high resolution (HR-EI) using perfluorokerosene (PFK) as an internal standard. The molecular ion of compound I was observed at m/z 380. Scanning high resolution EI mass measurements suggested a molecular formula of $C_{21}H_{32}O_6$; found 380.2187, calculated 380.2199.

$^1$H and $^{13}$C NMR spectra were recorded at 500 MHz or 125 MHz respectively at 25° C. on a Varian Unity 500 spectrometer equipped with a Nalorac micro-inverse detection probe. Chemical shifts are reported in ppm downfield from TMS (tetramethylsilane) and spectra were referenced to the solvent peak (3.30/49.0 ppm, $^1$H/$^{13}$C).

EXAMPLE 2
Fermentor Bioconversion of Sordarin

A frozen glycerol suspension of Actinomyces spp. MA7235 was inoculated into 25 ml of the preferred production medium (BASA, pH 7.0) in a 250 ml flask, incubated aerobically for three days at 29° C. on a rotary shaker operated at 200 rpm. The 25 ml 3 day primary seed was passed to 600 ml of fresh production medium and grown for an additional day to generate a second stage seed. The second stage seed culture was inoculated to a 23 liter Chemap fermentor batched with 15 liters of production medium (BASA) to which 1 g/L of polyethylene glycol P2000 was added as an antifoaming agent. The temperature of the fermentor was controlled at 29° C. and the culture was agitated at 400 rpm. Sordarin was dissolved in 80% ethanol and added to the fermentor at concentrations of either 0.25 g/L or 0.5 g/L. The 0.25 g/L run was charged with substrate at 22 hours post inoculum and the 0.50 g/L run was charged at 20 hours post inoculum. The batches were mixed with an equal volume of methanol and stored at 4° C. The pH of the culture at the time of addition was between 7.2 and 8.0 and Compound I was produced during the 12 hour period postcharge as determined by the same HPLC criteria as detailed in example 1.

EXAMPLE 3
Isolation of Compound I

Broth from two 23 liter fermentors prepared as described in Example 2 was extracted with an equal volume of methanol. The extract was diluted with H$_2$O and adjusted to pH 3 with conc. H$_3$PO$_4$. The solution was adsorbed onto a 2 liter column of Mitsubishi SP207 in upflow mode at a flow rate of 400 mL/min. After adsorption the column was washed with 20 liters of a solution of methanol/H$_2$O (1:4). Crude Compound I was eluted from the resin with a solution of methanol/H$_2$O (4:1). Fractions 2–5, one liter each, contained Compound I. Fractions 2–5 were combined and concentrated in vacuo to 1 liter. The solution was diluted with 1 liter of H2O and adjusted to a pH of approx. 11 by adding 40 mL of 5.0 N NaOH. This solution was extracted twice with an equal volume of EtOAc. The pH of the aqueous layer was adjusted to pH 2.5 with conc. H$_2$SO$_4$ and extracted twice with an equal volume of EtOAc. The EtOAc layers were combined and washed once with H$_2$O, once with brine and dried over anhydrous Na$_2$SO$_4$. The Na$_2$SO$_4$ was removed by filtration and the solution concentrated in vacuo.

Crude Compound I from above was further purified by column chromatography on silica gel 60 (E. Merck, 230–400 mesh, 750 mL). The column was equilibrated with a solution of EtOAc containing 1% glacial acetic acid and eluted at 25 mL/min. Fractions, 25 mL each, were collected and Compound I was recovered in 87–133. Final purification of Compound I could be accomplished by preparative RP HPLC on Phenomenex Primesphere C8 using a mobile phase consisting of methanol/H$_2$O (1:1) containing 0.1% H$_3$PO$_4$. Final purification of Compound I as the potassium salt was accomplished by conversion to the potassium salt and crystallization from a mixture of isopropanol:acetonitrile (1:2).

The following examples illustrate representative compositions containing Compound I.

EXAMPLE A 1000 compressed tablets each containing 500 milligrams of Compound I are prepared from the following formulation:

|  | grams |
|---|---|
| Compound I | 500 |
| Starch | 750 |
| Dibasic calcium phosphate hydrous | 5000 |
| Calcium stearate | 2.5 |

The finely powdered ingredients are mixed well and granulated with 10 percent starch paste. The granulation is dried and compressed into tablets.

EXAMPLE B 1000 hard gelatin capsules, each containing 500 milligrams of Compound I are prepared from the following formulation:

|  | grams |
| --- | --- |
| Compound I | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE C 250 milliliters of an injectible solution are prepared by conventional procedures from the following formulation:

| Dextrose | 12.5 | grams |
| --- | --- | --- |
| Water | 400 | milligrams |
| Compound I | 250 | milliliters |

The ingredients are blended and sterilized for use.

EXAMPLE D

An ointment suitable for topical application may be prepared by intimately dispersing 13 mg of Compound I in 1 g of commercially available polyethylene/hydrocarbon gel.

EXAMPLE E

An aerosol composition may be prepared having the following formulation (per canister):

| Compound I | 24 mg |
| --- | --- |
| Lecithin NF, liquid concentrate | 1.2 mg |
| Trichlorofluoromethane | 4.025 g |
| Dichlorodefluoromethane | 12.15 g |

While the foregoing specification teaches the principles of the present invention, it will be understood that the practice of the invention encompasses all of the casual variations, adaptations, modifications, deletions, or additions of procedures and protocols described herein, as come within the scope of the following claims and its equivalents.

What is claimed is:

1. A compound of the formula

2. A process for the preparation of the compound of claim 1 which comprises a. contacting a compound of the formula with Actinomyces spp. MA7235, ATCC No. 202103 or a mutant which retains the capability of performing the process, thereof; and b. isolating the compound of claim 1.

3. An antifungal composition comprising an amount of the compound of claim 1 sufficient to exert an antifungal activity and a biologically inert carrier or diluent therefor.

4. The antifungal composition according to claim 3 wherein the carrier is a pharmaceutically acceptable carrier.

5. A method of treating fungal infections in mammals comprising administering to a patient in need thereof an amount sufficient to exert an antifungal activity of the compound of claim 1.

6. A method for treating agricultural fungal infections which comprises administering to the site where growth is to be treated an amount sufficient to exert an antifungal activity of the compound of claim 1.

7. A biologically pure culture of bacteria (ATCC 202103) capable of transforming sordarin to 11-hydroxysordarin.

* * * * *